United States Patent
West et al.

(10) Patent No.: US 6,500,119 B1
(45) Date of Patent: Dec. 31, 2002

(54) OBTAINING IMAGES OF STRUCTURES IN BODILY TISSUE

(75) Inventors: Alan I. West, Hopkinton, MA (US); David Krag, Shelburne, VT (US); Joel B. Weinstein, Framingham, MA (US); Navin Dewagan, Milford, MA (US)

(73) Assignee: Medical Tactile, Inc., Los Angeles, CA (US)

(*) Notice: Subject to any disclaimer, the term of this patent is extended or adjusted under 35 U.S.C. 154(b) by 0 days.

(21) Appl. No.: 09/452,913

(22) Filed: Dec. 1, 1999

(51) Int. Cl.[7] .............................. A61B 8/00; A61B 5/103
(52) U.S. Cl. ..................... 600/437; 600/443; 600/587
(58) Field of Search ............................. 600/463, 587, 600/10, 445, 437, 566, 407, 568, 424, 439, 471, 440, 459, 442; 604/4.01

(56) References Cited

U.S. PATENT DOCUMENTS

| | | | |
|---|---|---|---|
| 4,856,993 A | 8/1989 | Maness et al. ................. 433/68 |
| 5,099,848 A | 3/1992 | Parker et al. | |
| 5,265,612 A | 11/1993 | Sarvazyan et al. | |
| 5,394,875 A * | 3/1995 | Lewis et al. ................. 600/445 |
| 5,524,636 A | 6/1996 | Sarvazyan et al. | |
| 5,678,565 A | 10/1997 | Sarvazyan | |
| 5,785,663 A | 7/1998 | Sarvazyan | |
| 5,797,849 A | 8/1998 | Vesely et al. | |
| 5,989,199 A * | 11/1999 | Cundari et al. ............. 600/587 |
| 6,083,170 A * | 7/2000 | Ben-Haim ................... 600/463 |
| 6,200,310 B1 * | 3/2001 | Ben-Haim et al. ............ 606/10 |

FOREIGN PATENT DOCUMENTS

| | | |
|---|---|---|
| EP | 0920833 | 6/1999 |
| WO | WO 97/17017 | 5/1997 |
| WO | WO 98/26269 | 6/1998 |

* cited by examiner

Primary Examiner—Francis J. Jaworski
Assistant Examiner—Ruby Jain
(74) Attorney, Agent, or Firm—Wolf, Greenfield & Sacks, P.C.

(57) ABSTRACT

An apparatus obtains image data for a structure through bodily tissue. The apparatus includes an imaging sensor that contacts the bodily tissue to obtain image data for a first image of the structure. A pressure sensor is oriented in substantially a same direction as the imaging sensor and contacts the bodily tissue to obtain data for a second image of the structure. The second image is a different perspective of the structure than the first image.

35 Claims, 19 Drawing Sheets

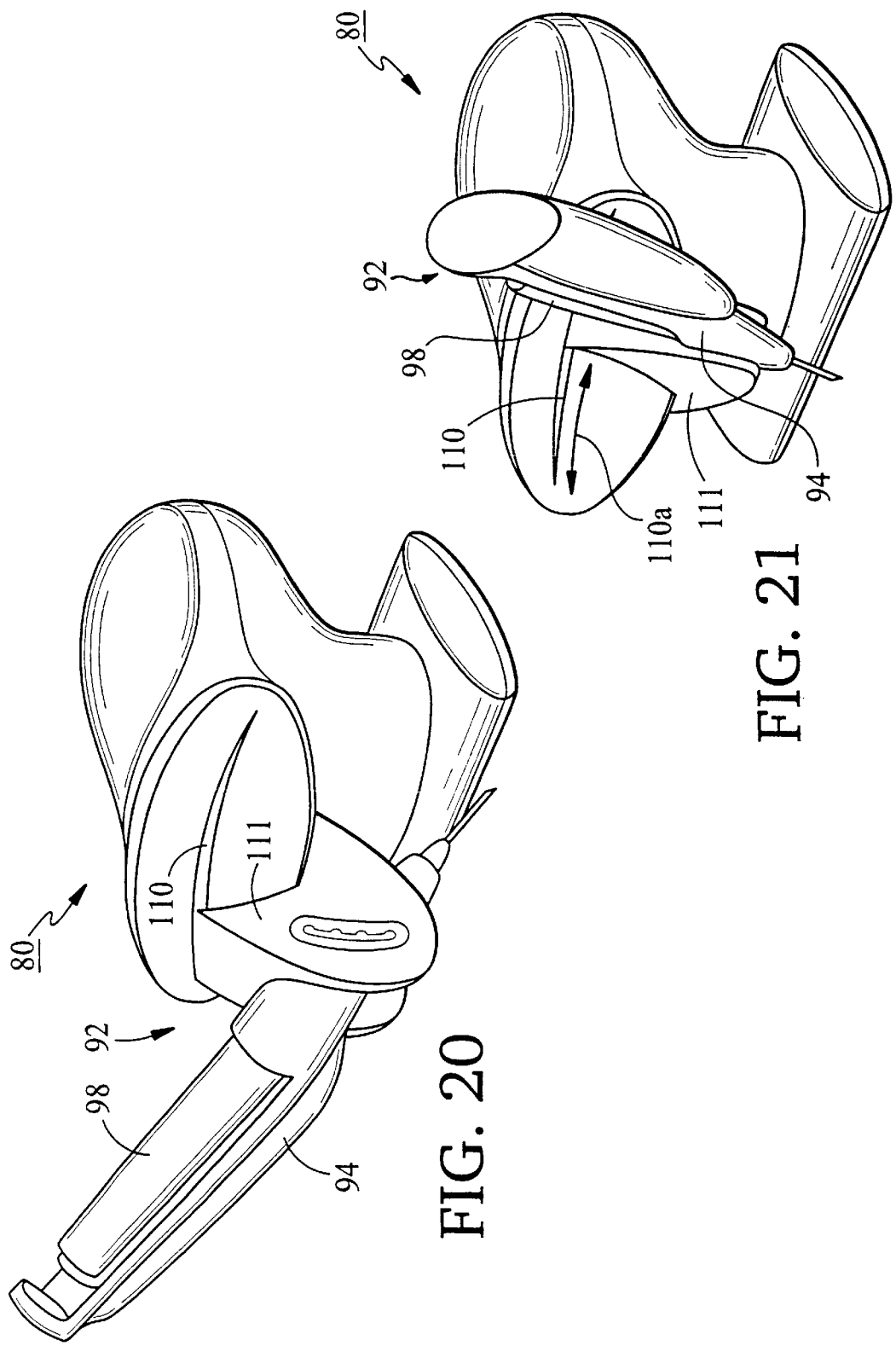

OBTAINING IMAGES OF STRUCTURES IN BODILY TISSUE

BACKGROUND OF THE INVENTION

This invention relates to obtaining images of structures, such as tumors or lesions, in bodily tissue.

Modern imaging techniques have reduced the need for major surgical procedures to identify foreign structures in bodily tissue. For example, pressure sensors can be used to obtain a topographic image of bodily tissue and to determine the "hardness" (or density) of a structure in the tissue based on an amount of resistance provided by the structure. If the structure is relatively hard, it is more likely to be malignant, whereas if the structure is relatively soft, it is less likely to be malignant.

Ultrasound is another imaging technique that is used to obtain images of bodily tissue. Ultrasound provides narrow, cross-sectional slices of bodily tissue which make it possible, in some cases, to distinguish between benign and malignant tumors without major surgery. Readings from ultrasound devices are dependent upon the location and pressure applied to the ultrasound device.

For example, in breast cancer diagnoses, a technique known as "elastography" is implemented using ultrasound. According to this technique, while a structure is being examined, an ultrasound scanning head is pressed into the breast causing a compressive load on the structure and its surrounding tissue. By noting the relative change in the structure's size as more load is applied, a user can make a qualitative assessment of how hard the structure is, with the assumption that a hard structure is more apt to be malignant. This same procedure can be repeated to determine if a structure has changed since a previous examination.

SUMMARY OF THE INVENTION

In general, in one aspect, the invention features obtaining image data for a structure through bodily tissue. An imaging sensor contacts the bodily tissue to obtain the image data for the structure. A pressure sensor is oriented in a substantially same direction as the imaging sensor. The pressure sensor contacts the bodily tissue to produce a signal that corresponds to an amount of pressure between the pressure sensor and the bodily tissue.

Among the advantages of this aspect of the invention may be one or more of the following. In order to determine if the consistency and/or size of a structure has changed between examinations, it is important to ensure that the pressure and orientation of sensors in a subsequent examination is similar to the pressure and orientation of sensors in a previous examination. The pressure sensor provides a way of doing this. For example, the pressure sensor can be used to measure an amount of pressure at a particular orientation of the imaging sensor. This pressure can then be duplicated during a subsequent examination, thereby providing more reliable examination results.

This aspect of the invention may include one or more of the following features. The imaging sensor is an ultrasound transducer. The pressure sensor is part of an array of pressure sensors and the imaging sensor is part of an array of imaging sensors. The array of pressure sensors is arranged at locations along an outer perimeter of the array of imaging sensors. Each pressure sensor produces a signal that is indicative of an amount of pressure between the pressure sensor and the bodily tissue. A processor analyzes signals from the pressure sensors to determine if an orientation of the pressure sensors is the same as a previous orientation of the pressure sensors.

A device may be included which provides an indication of the amount of pressure between the pressure sensor and the bodily tissue based on the pressure signal. The device comprises circuitry which receives the signal from the pressure sensor and the image data obtained by the imaging sensor, and which generates the indication and an image of the structure. The indication can comprise a visual indication and may be implemented using one or more light-emitting diodes which illuminate in accordance with the signal. Alternatively, the visual indication may be a computer monitor or other display device. The indication can comprise an audio indication, such as an audible tone that varies in accordance with the signal. This aspect of the invention may be incorporated into one of, e.g., an ultrasonic endoscope, a laparoscope, a transesophogeal ultrasonic endoscope, an intravascular catheter, an ultrasonic gastric endoscope, a duodenoscope, and a colonoscope.

In general, in another aspect, the invention features obtaining image data for a structure through bodily tissue. An imaging sensor contacts the bodily tissue to obtain image data for a first image of the structure. A pressure sensor is oriented in a substantially same direction as the imaging sensor, which contacts the bodily tissue to obtain data for a second image of the structure. The second image is a different perspective of the structure than the first image.

Among the advantages of this aspect of the invention may be one or more of the following. The two images provide a user with views of different perspectives of the structure. For example, the pressure sensors may provide a topographic view which identifies relatively hard regions of the structure. The imaging sensors may provide cross-sectional slices of the structure. Thus, with the slices and the topographic view, the user is able to view the structure in three dimensions, and make a more informed decision as to whether the structure is likely to be benign or malignant. It is also possible to determine the relationship between depth and hardness and to use this information to gain further knowledge of the structure. For example, the same structure may appear to have different hardnesses depending upon its depth. Knowing the depth of the structure, therefore, can correct this discrepancy.

This aspect of the invention may include one or more of the following features. The imaging sensor may comprise an ultrasound transducer, in which case the first image comprises a cross-sectional slice of the structure. The second image comprises a topographic map of the structure. The topographic map shows areas of the structure having different characteristics in different shades. An example of different characteristics includes different levels of hardness in the structure.

The pressure sensor may be part of an array of pressure sensors and the imaging sensor may be part of an array of imaging sensors. The pressure sensors may be arranged at locations along an outer perimeter of the imaging sensors. For example, the pressure sensors may be arranged to surround the imaging sensors.

A display screen displays the first and second images at a same time and an identifier that identifies the second image. A processor receives the data for the first and second images from the imaging sensor and pressure sensor, respectively, and processes the data to generate the first and second images for display on the display screen.

In general, in another aspect, the invention features obtaining image data for a structure through bodily tissue. In this aspect, a pressure sensor contacts the bodily tissue to obtain data for the structure and a position tracking device determines a location of the pressure sensor relative to the structure.

Among the advantages of this aspect of the invention may be one or more of the following. Knowing the location of the pressure sensor relative to the structure makes it possible to identify a specific region of the structure for re-examination and to control placement of the pressure sensors on the bodily tissue accordingly. Imaging sensors may also be included to obtain image data for a different image of the structure. The imaging sensors may be positioned in accordance with the location determined by the position tracking device, making re-examination more precise.

This aspect of the invention may include one or more of the following features. An imaging sensor is included that contacts the bodily tissue to obtain image data for a different image of the structure. The imaging sensor comprises an ultrasound transducer. The pressure sensor is part of an array of pressure sensors that are arranged along an outer perimeter of the imaging sensor. A display screen displays the image of the structure and an image of the apparatus relative to the structure based on the data.

The position tracking device obtains data for a body containing the structure. The display screen displays an image that is representative of the body and a location of the structure relative to the body based on the data. The position tracking device obtains the image data for the body and the location of the structure relative to the body based on fiducial points in the body.

In general, in another aspect, the invention features obtaining information relating to a structure through bodily tissue. An imaging sensor contacts the bodily tissue to obtain first information relating to the structure. A pressure sensor is oriented in a substantially same direction as the imaging sensor. The pressure sensor contacts the bodily tissue to obtain second information relating to the structure. The second information differs from the first information.

Among the advantages of this aspect of the invention may be one or more of the following. Obtaining different information about a structure facilitates identification and removal of the structure. For example, the first information may relate to a hardness of the structure and the second information may relate to a depth of the structure within the bodily tissue. This information can be used in classifying the structure as benign or malignant and, if necessary, removing the structure from the tissue.

This aspect of the invention may include one or more of the following features. The imaging sensor comprises an A-mode ultrasound transducer. A display, such as a monitor, displays the first information and the second information. A fixture guides a tissue sampling device to the structure. The fixture is movable (both vertically and horizontally) over a range of angles.

Other features and advantages will become apparent from the following description, claims, and drawings.

BRIEF DESCRIPTION OF THE DRAWINGS

FIGS. 20 and 21 are perspective views of the tissue sampling device attached to the fixture.

DESCRIPTION

Figure 1:
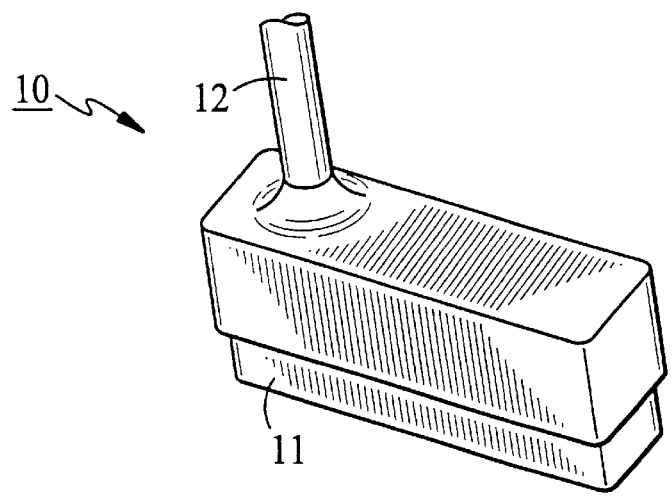
FIG. 1 is a perspective view of a scanning head of a tissue examination device.
Figure 2:
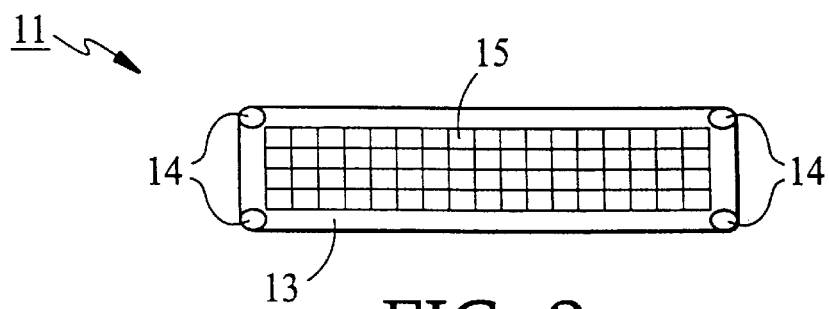
FIG. 2 is a front view of a sensor array on the scanning head, including ultrasound and pressure sensors.

Referring to FIG. 1, a tissue examination device 10 includes a scanning head 11 and a handle 12. Handle 12 is grasped by a user to place scanning head 11 against bodily tissue being examined, such as a breast. The face of scanning head 11 (FIG. 2) includes an array of imaging sensors 15 and pressure sensors 14 mounted on a membrane surface 13 such that the imaging and pressure sensors are oriented in substantially the same direction. The imaging sensors are ultrasound transducers in this embodiment; however, other types of imaging sensors may be used. The pressure sensors are arranged at locations along an outer perimeter of the imaging sensors. For example, four pressure sensors 14 are arranged around the outer perimeter of imaging sensors 15, as shown in FIG. 2.

1. Obtaining Pressure Information Using Pressure Sensors

Figure 3:
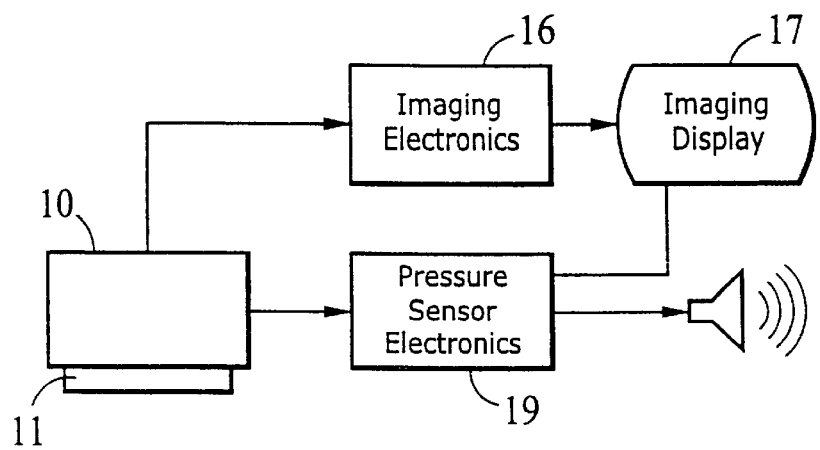
FIG. 3 is a block diagram of electronics for interpreting information from the sensor array.

Referring to FIG. 3, imaging sensors (hereinafter "ultrasound transducers") 15 contact external bodily tissue, such as a breast, that is the subject of an examination. In use, scanning head 11 is manually pressed against and translated across the skin by applying pressure via handle 12. The translation technique is essentially a translation of head 11 over time to allow a user to increase breast area coverage with less examination time.

Figure 4:
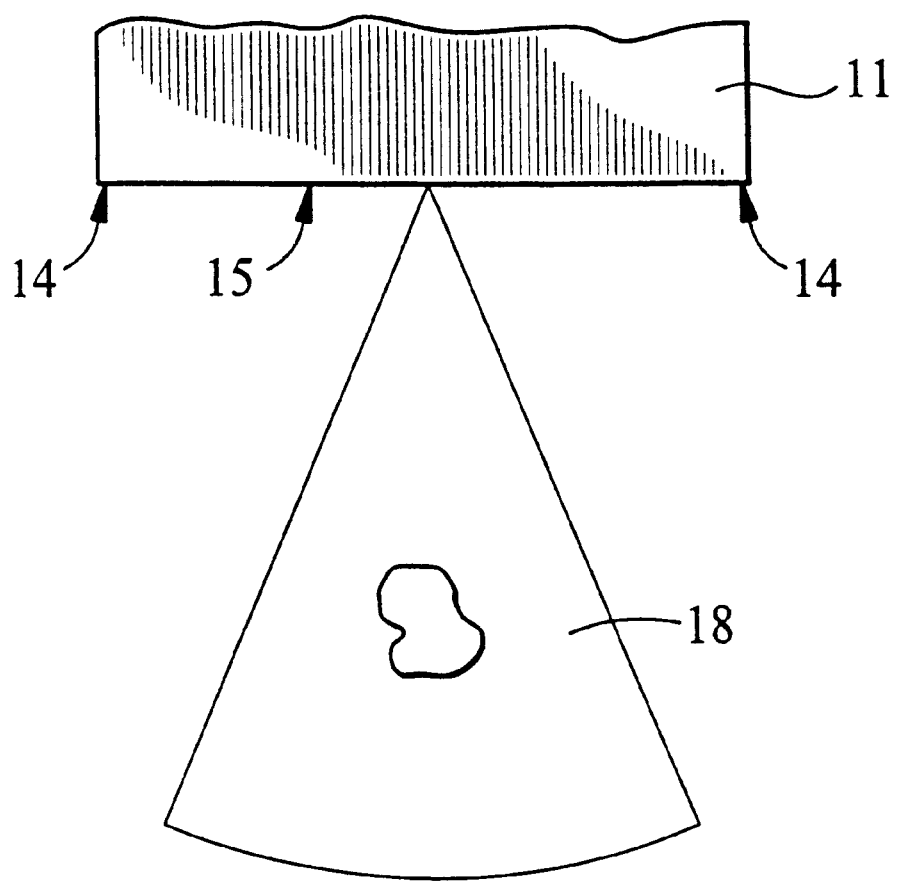
FIG. 4 is a view of an ultrasound image.

Ultrasonic waves in the range of roughly 2.25 to 10 megahertz ("MHz") are transmitted from ultrasound transducers 15 through skin and underlying tissues and structures. Echoes of these ultrasonic waves are detected by ultrasound transducers 15 and measured by imaging electronics 16. The resulting measurements are A/D (analog-to-digital) converted to obtain image data. The image data defines a cross-sectional slice of underlying tissue, including structures such as tumors. As shown in FIG. 4, a cross-sectional slice 18 is an image of the tissue that is roughly orthogonal to imaging sensors 15.

Imaging electronics 16 is a computer or other processing device which receives signals obtained via ultrasound transducers 15 and which processes those signals to obtain image data for the ultrasound images. Imaging electronics 16 includes a display screen 17 (or other displaying device) for viewing the ultrasound images. Other types of images may also be viewed on display screen 17, as described in more detail below.

Pressure sensors 14 comprise, for example, contact sensors such as those described in U.S. Pat. No. 4,856,993, entitled "Pressure and Contact Sensor System for Measuring Dental Occlusion" and filed on Nov. 27, 1996; U.S. patent application Ser. No. 08/931,573, entitled "Clinical Tissue Examination" and filed on Sept. 16, 1997; and U.S. patent application Ser. No. 08/950,167, entitled "Diagnosis And Treatment Of Tissue With Instruments" and filed on Oct. 14, 1997, all three of which are incorporated herein by reference. Pressure sensors 14 are resistive elements that are relatively small and closely-spaced to provide high resolution capable of distinguishing between areas of underlying tissue separated by 1 mm or less. The resistance of each pressure sensor 14 changes in accordance with the amount of pressure applied to that sensor. This resistance change is inversely proportional to the pressure imposed on each sensor. Thus, the resistance of each sensor decreases as applied pressure increases.

The pressure imposed on pressure sensors 14 increases when they are pressed against localized areas of stiffer tissue on, within, or below softer breast tissue. Examples of such stiffer tissue include normal breast tissue structures—such as the nipple, the inframammary ligament, and ribs—and foreign bodies such as cysts and solid masses (whether or not pathogenic). Consequently, as scanning head 11 is pressed and moved against the breast, the pressure imposed on pressure sensors 14, and thus the resistance of pressure sensors 14, varies in accordance with the properties of structures in the underlying tissue.

Figure 5:
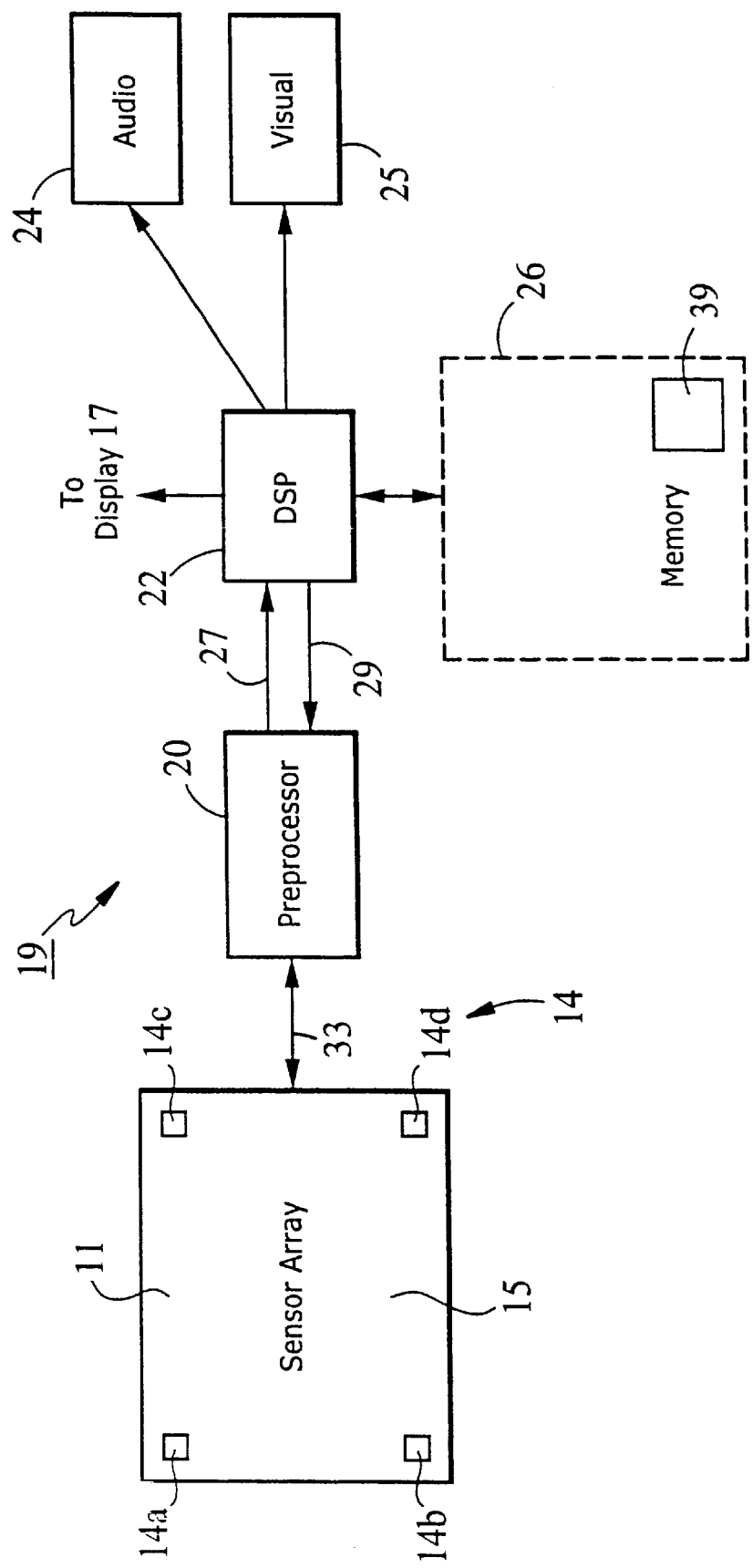
FIG. 5 is a block diagram of pressure sensing electronics included in the electronics of FIG. 3.

Pressure sensor electronics 19 is a computer or other processing device. For example, pressure sensor electronics 19 may be implemented in the same computer as imaging electronics 16. As shown in FIG. 5, pressure sensor electronics 19 includes preprocessor 20, digital signal processor ("DSP") 22, audio and visual indicators 24 and 25, respectively, and memory 26. Features of this circuitry are described allowed U.S. patent application No. 08/757,466, entitled "Tissue Examination", the contents of which are incorporated herein by reference.

The individual resistances of pressure sensors 14 are read by preprocessor 20, the output 27 of which is applied to DSP 22 (other processors may be used instead of, or in addition to, a DSP). Preprocessor 20 sequentially measures the resistance of pressure sensors 14 in response to row and column address signals 29 provided by DSP 22 to provide an indication of pressure applied to the pressure sensor at that row and column address. During each resistance measurement, preprocessor 20 applies a reference potential (not shown) to an addressed sensor 14, measures the voltage drop induced across that sensor, and generates an output 27 corresponding to the voltage drop. Thus, each pressure sensor 14 produces a signal (in this example, resistance-induced voltage) in response to the applied pressure.

These signals 33 are indicative of the amount of pressure applied to the corners of scanning head 11 during an examination. They are A/D (analog-to-digital) converted and processed using DSP 22 to obtain the amount of pressure applied to each pressure sensor during the current examination. This information is compared to data that is pre-stored, e.g., in memory 26, in order to determine if the sensed pressure is within a range specified by that data.

The information also may be stored in memory 26 and indexed to information relating to the current examination. For example, a patient identifier may be stored with the pressure information, together with the time and date of the examination. During a subsequent examination of the patient, the patient identifier may be entered, and the pressure information for that patient retrieved. This pressure information can be used to ensure that the amount of pressure applied for the current examination, and the way in which that pressure is applied (e.g., the orientation of scanning head 11) is the same, or similar to, the pressure and orientation applied during the previous examination.

By way of example, if pressure sensors 14a and 14b (FIG. 5) reported higher levels of pressure than pressure sensors 14c and 14d during a first examination, this information could be used to ensure that those pressure amounts are repeated during a second examination. Thus, the circumstances of the second examination (e.g., scan head orientation) can be made to substantially match the circumstances of the first examination.

Figure 6:
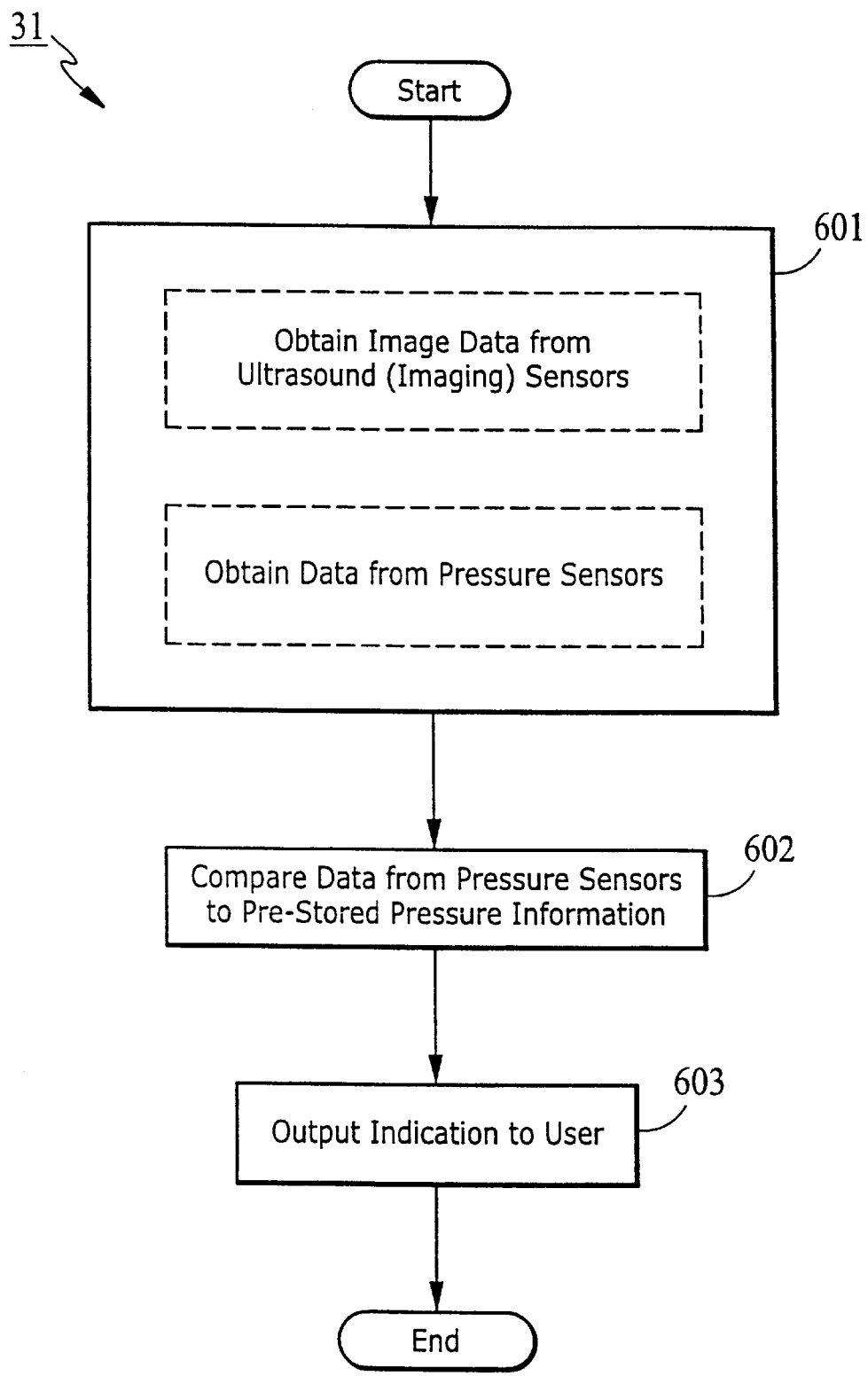
FIG. 6 is a flow diagram showing a process for obtaining images and pressure information using the scanning head of FIG. 1.

Referring to FIG. 6, a process 31 is shown for obtaining image data using device 10. In 601, image data is obtained for underlying tissue, including any structures therein, using imaging sensors 15. This is done by placing scanning head 11 against the skin of a patient and moving the scanning head across the skin's surface in an area near the underlying tissue. For example, in the case of a breast exam, the scanning head is placed against a portion of the breast to be imaged, and scanning head 11 is moved along the surface of the breast. Ultrasound images are formed on display 17 from data obtained by ultrasound transducers 15.

Also in 601, pressure sensors 14 produce signals that correspond to an amount of pressure between the breast and each corner of scanning head 11 during imaging (this may be performed before, during, or after image data is obtained by ultrasound transducers 15). For example, if an elastography procedure is being performed, the amount of pressure may be significant relative to a normal imaging procedure. Also, as noted, the pressure information is used to ensure that the orientation of scan head 11 is the same during previous and subsequent examination. The resulting signals are compared (602) (by DSP 22) to pre-stored pressure information. The results of the comparison are used to output (603) an indication relating to the amount of pressure measured by pressure sensors 14 as those amounts relate to the orientation of scan head 11 (e.g., whether the pressure at each pressure sensor 14 is within an acceptable tolerance of the pressure applied to that same sensor during a previous examination).

The indication may be audio or visual. For example, the indication may be an audible tone (output via audio indicator 24). The tone may increase in frequency as the amount of pressure deviates further from pre-stored pressure information. A visual indicator 25, such as light emitting diodes ("LEDs") or a computer display screen, may also be used. As with the audible tone, the illumination of the LEDs may increase in intensity based on the amount of pressure applied to scanning head 11. In still other embodiments, the amount of pressure applied to each pressure sensor 14 can be represented numerically and displayed on display screen 17 (along with an ultrasound image generated using data from ultrasound transducers 15).

Figure 7:
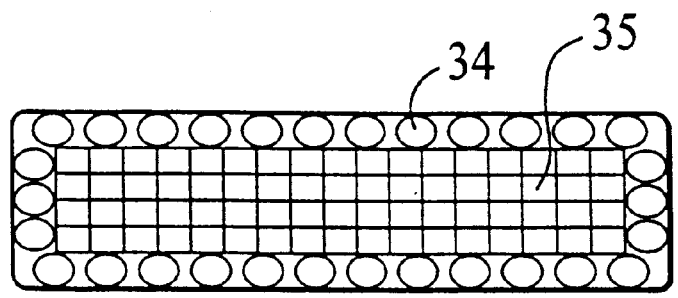
FIGS. 7, 8 and 9 are alternative configurations for the sensor array on the scanning head.
Figure 8:
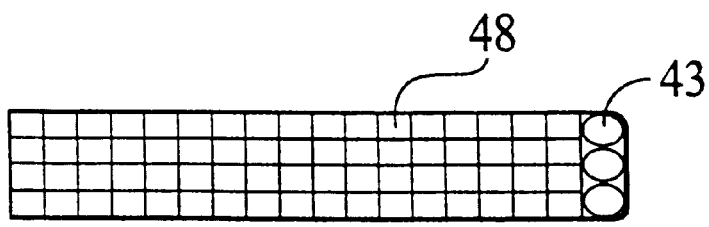
Figure 9:
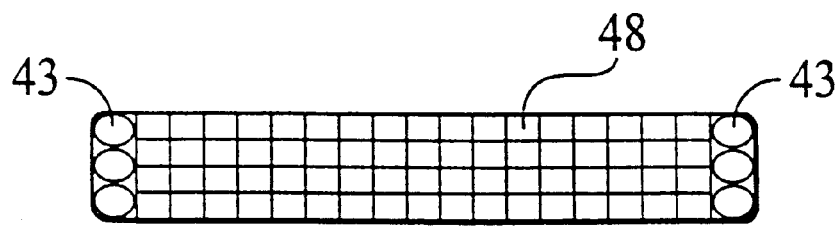

This embodiment is not limited to the particular configuration set forth herein. For example, indicators other than those described above may be used. Similarly, several indicators may be used in combination. Any number and arrangement of pressure sensors may be used. For example, as shown in FIG. 7, pressure sensors 14 may be arranged in a "picture frame" arrangement around imaging sensors 15. This arrangement provides additional pressure data for determining the orientation of scan head 11. Alternatively, as shown in FIGS. 8 and 9, respectively, pressure sensors 14 may be arranged in a linear array on one side of the imaging sensors 15 or on opposite sides of the imaging sensors. The arrangement of FIG. 9 provides more data than that of FIG. 2, but less than that of FIG. 7. The arrangement of FIG. 8 provides, essentially, only a two-dimensional look at the orientation of scan head 11. In other embodiments, the pressure sensors may be interspersed among the imaging sensors.

2. Obtaining Ultrasound and Pressure Images

In addition to measuring pressure using the pressure sensors (as above), it is also possible to construct images using data from the pressure sensors. Pressure sensor electronics 19 (FIG. 3) is used to construct such images.

The level of definition in a "pressure" image is related to the number of pressure sensors used to obtain pressure information. To obtain an image (as opposed to mere pressure data), at least one linear array of pressure sensors should be used. Larger numbers of pressure sensors provide more data, which can be used to produce images more quickly. For example, the "picture frame" arrangement of pressure sensors shown in FIG. 7 will obtain data more quickly than the arrangements shown in FIGS. 8 and 9. This embodiment of the invention is not limited to any specific arrangement; however, it is described with respect to the sensor arrangement shown in FIG. 7.

Referring to FIG. 5, in this embodiment, preprocessor 20 outputs signals 27, which are digitized by A/D converters (not shown) and applied to DSP 22 (alternatively, an input stage of DSP 22 may perform the A/D conversion). The set of sequentially produced output signals for all pressure sensors 14 (regardless of the pressure sensor configuration) is termed a "frame". DSP 22 addresses preprocessor 20 at a rate sufficient to read 8 frames or more of output signals 27 per second. DSP 22 stores each frame of signals 27 in an area memory 26. DSP 22 combines these frames, based on the locations from which they were obtained on the patient, to produce a topographic pressure map of structures in the underlying tissue.

Different types of tissue structures have different pressure signatures. These pressure signatures result from the way in which tissue structures respond to being stressed by pressure exerted when a user moves the scanning head over the breast. The hardness of a given tissue structure, its composition (e.g., percentage of fat, presence of ducts, and fibrous tissue), and the degree to which the tissue structure is held in place by surrounding tissue are all factors that contribute to the pressure signature of the tissue structure. Another factor which affects the pressure signature is whether anatomical structures, such as ribs, lie beneath the tissue. These factors, in combination, are sufficiently different for various types of tissue structures (e.g., normal breast structures, such as ribs, nipples, and ligaments, and foreign structures, such as cysts and solid masses) that pressure signatures of such structures are distinguishable from each other.

As described in detail in allowed U.S. patent application Ser. No. 08/757,466, entitled "Tissue Examination", incorporated by reference above, various processing tests (defined, e.g., by an operating program 39 stored in memory 26) are performed on the topographic map stored in memory 26. These tests enable DSP 22 to discriminate underlying tissue structures from potentially foreign structures. This information is used to eliminate known underlying structures, such as bones, from images, thus making it easier to identify foreign structures, such as tumors.

Knowing the depth of the structure using ultrasound, it is also possible to account for pressure differences caused by differences in the depth of the structure in the breast. For example, a structure deep in the breast may seem less hard to the pressure sensors than that same structure near the surface of the breast. Taking into account the depth of the structure, it is possible to correct for these apparent differences in hardness.

Figure 10:
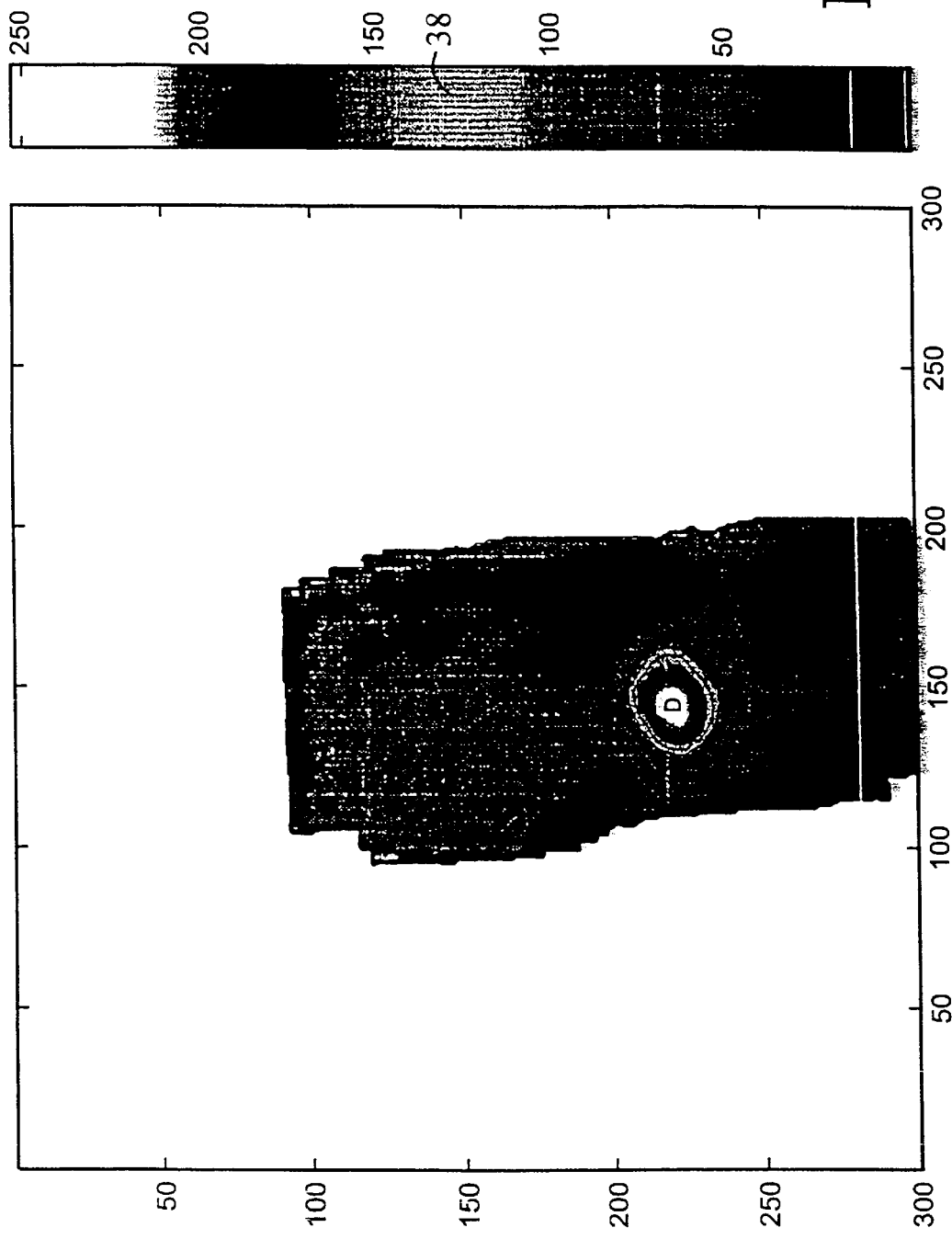
FIG. 10 is a view of a topographic map generated from information obtained by the pressure sensors.

The topographic map stored in memory 26 is a three-dimensional ("3D") image of underlying tissue and structures. FIG. 10 shows an example of such a topographic map. Because the image is a topographic map of a 3D image, it essentially appears as a two-dimensional ("2D") image with the third dimension being shown by a shading (e.g., colors) that correlate to the varying strengths with which tissue pushes back in response to imposed pressure. Pressure information from sensors 34 is used to generate the shading that represents the third dimension of the topographic map. A shading pressure scale 38 may be provided with the 3D image in which ranges of pressure information are defined and each range is assigned a specific color. The 3D image may also be graphically manipulated and displayed in other ways so as to provide further helpful visual cues. Alternatively, the topographic map could be a 3D image (meaning that it is shown in xyz coordinate space) with different hardnesses shown in different shadings, such as colors.

Figure 11:
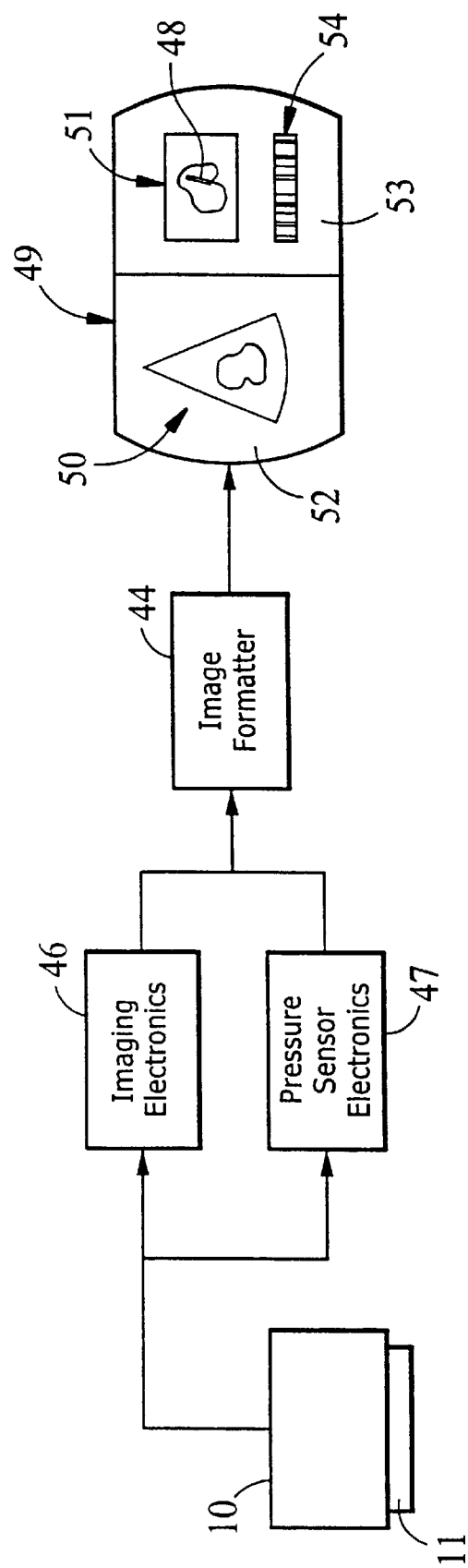
FIG. 11 is a block diagram of electronics for generating the topographic map and displaying the map alongside an ultrasound image.
Figure 26:
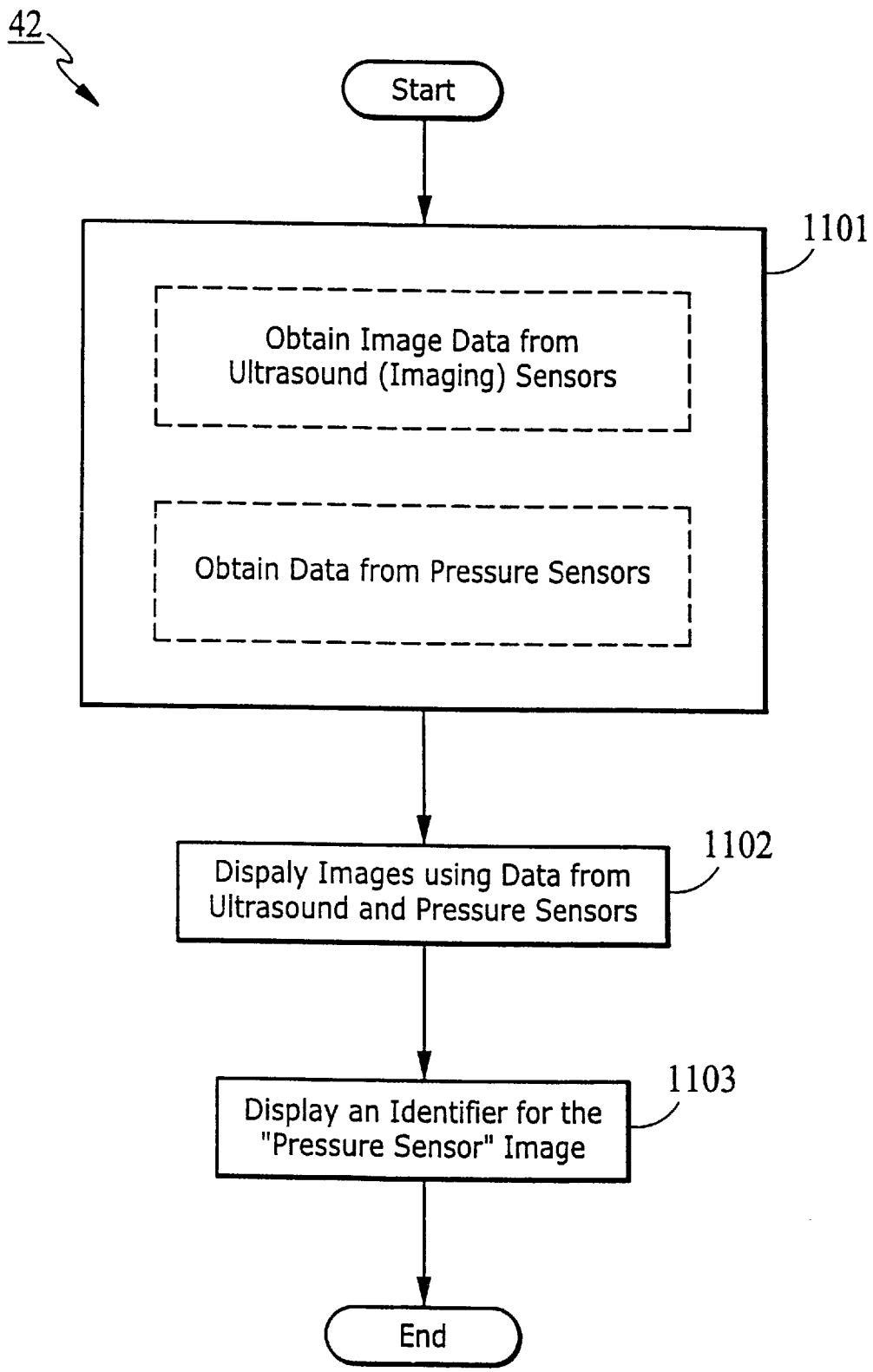
FIG. 26 is a flow diagram showing a process for obtaining ultrasound and "pressure" images using the electronics of FIG. 11.

FIG. 26 shows a process 42 for obtaining data from both ultrasound transducers 15 and pressure sensors 14 and for displaying images based on that data. In 1101, imaging electronics 46 (FIG. 11) obtains image data for ultrasound images using device 10. Imaging electronics 46 forms ultrasound images using this data, as described above. To reiterate, ultrasound images are cross-sectional slices of underlying tissue (including structures) taken along an axis that is roughly orthogonal to the imaging sensors.

Also in 1101, pressure sensor electronics 47 (which includes the components of FIG. 5) obtains pressure information from pressure sensors 14 and forms a topographic map of the underlying tissue. An image formatting routine 44 formats the ultrasound image and the topographic map for display on display screen 49. Image formatting routine 44 may run on the same computer that includes the imaging electronics and pressure sensing electronics. The ultrasound image 50 and topographic map 51 (both showing underlying structures in the tissue) are displayed in side-by-side, split screen areas 52 and 53 of the display. The location 48 of cross-sectional image 50 may also be identified on topographic map 51. This location shows from where on the patient cross-sectional image 50 was taken. Portions of topographic map 51 that indicate relatively hard tissue can be re-examined using ultrasound and the resulting ultrasound images can be re-displayed in area 52.

Area 53 may also include an identifier 54 that identifies topographic map 51. For example, in FIG. 11, identifier 54 may indicate (in words or otherwise) that topographic map 51 was obtained using pressure sensors. A similar indicator (not shown) may be provided in area 52 to indicate that image 52 is an ultrasound image.

This embodiment of the invention is not limited to the specific configuration set forth above. The invention is not limited to the specific hardware configurations shown in FIGS. 5 and 11. Any hardware, or combination of hardware and software, may be used. Also, the invention can be used with images other than pressure and/or ultrasound images.

Figure 27:
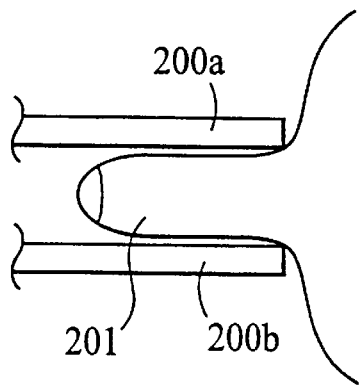
FIG. 27 is a side view of a mammography plates compressing a patient's breast.
Figure 28:
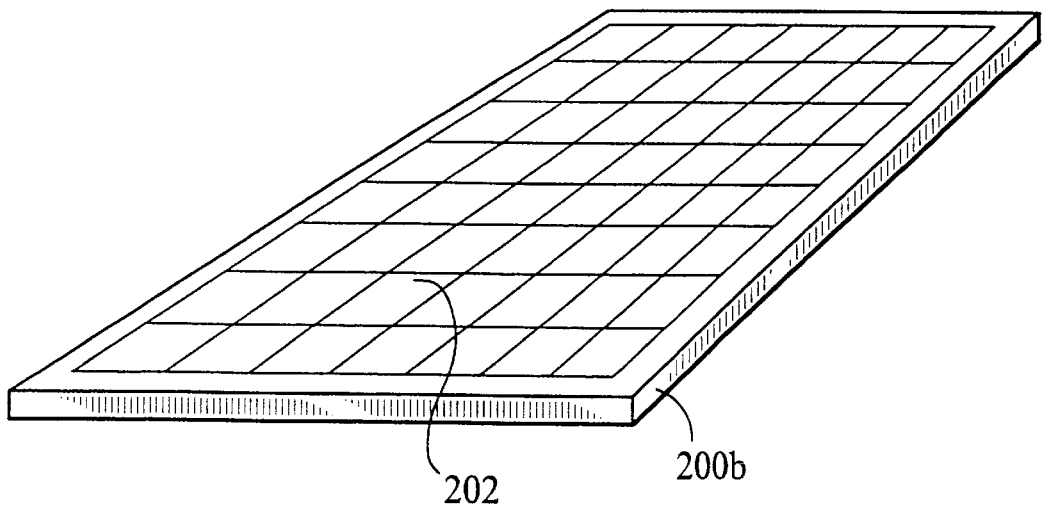
FIG. 28 is perspective view of a bottom mammography plate which includes pressure sensors.

Referring to FIG. 27, pressure sensors could be affixed to mammography plates 200a and 200b which compress breast 201. As shown in FIG. 28, radio-lucent pressure sensors 202 could be affixed to bottom plate 200b and/or to top plate 200a (FIG. 27). These pressure sensors are used to "visualize" palpable structures and the mammography plates are used to visualize non-palpable structures. The pressure sensors 202 could be dispersed throughout the mammography plates as shown or arranged in configurations similar to those of FIGS. 2 and 7 to 9.

Figure 29:
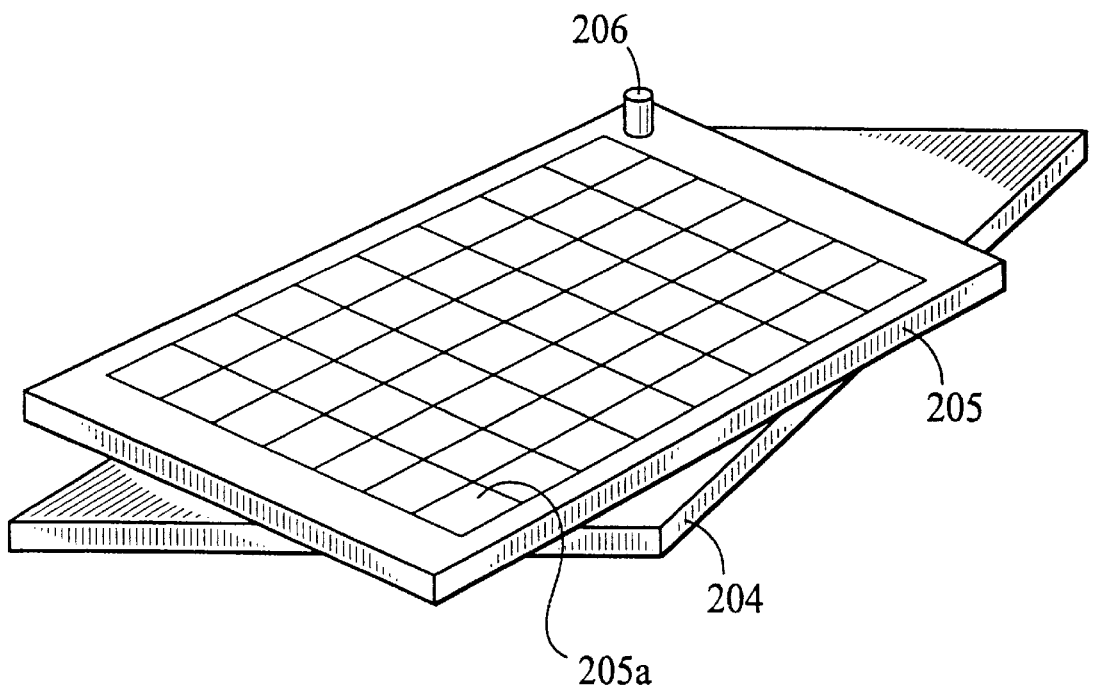
FIG. 29 shows rotatable pressure sensor and mammography plates.

FIG. 29 shows rotatable pressure sensor and mammography plates. This combination of plates may be used as the top and/or bottom plates in a mammography procedure. In this configuration, pressure sensor plate 205 includes pressure sensors 205a, which could be dispersed throughout the mammography plates as shown or arranged in configurations similar to those of FIGS. 2 and 7 to 9. Pressure sensor plate 205 pivots about rotating pin 206 relative to mammography plate 204. Mammography plate 204 is a standard mammography plate which takes mammograms of breast tissue. By providing rotation between the two plates, it is possible to position the plates so as to obtain pressure/mammogram images of specific breast tissue.

3. Using a Position Tracking Device

Figure 12:
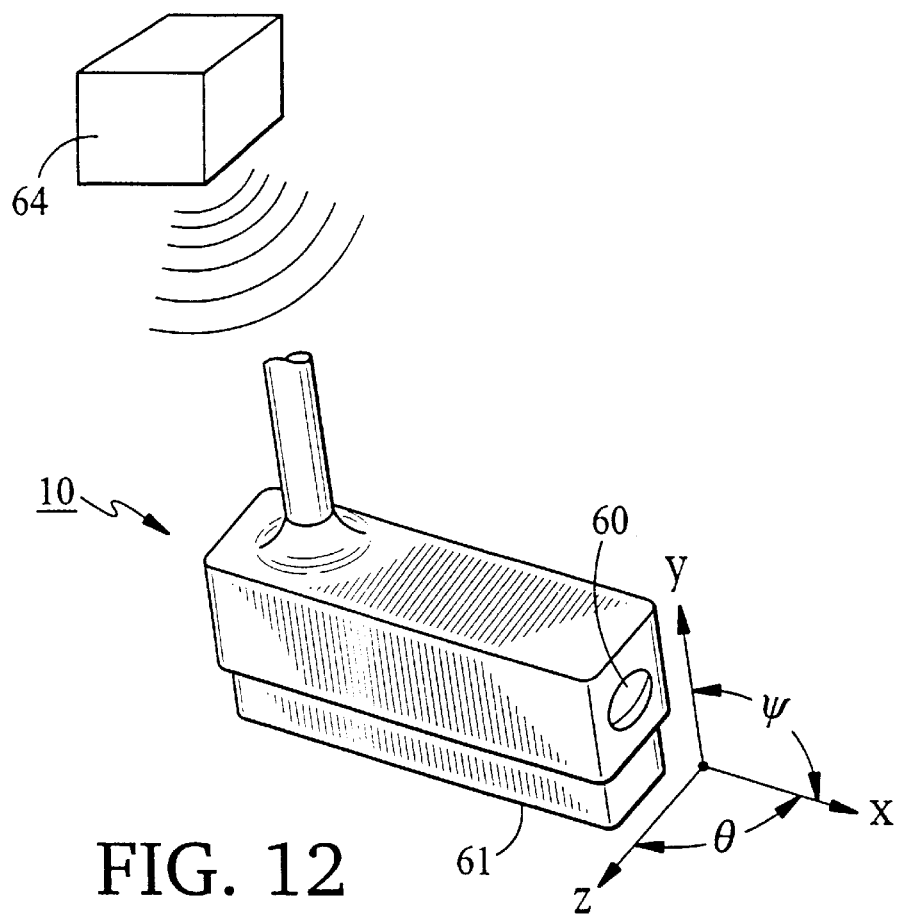
FIG. 12 is a perspective view of a scanning head which includes a position tracking device.

Referring to FIG. 12, this embodiment of the invention incorporates a position tracking device 60 into tissue examination device 10 of FIG. 1. Position tracking device 60 is a magnetic device that uses feedback to obtain the position of scanning head 61 (which includes pressure sensors 14 and ultrasound transducers 15) relative to underlying tissue structures (and even the body of a patient). Other types of position tracking devices that may be used include charge-coupled devices (CCDs) with infrared tracking and ultrasound position tracking.

Position tracking device 60 tracks up to six degrees of freedom, including (in Cartesian coordinate space), the xyz coordinates and angles between each of the axes and the detected structure. Position tracking device 60 determines the position of scanning head 61 based on a signal from a transmitter 64, which acts as a stationary reference point for position tracking device 60.

Figure 13:
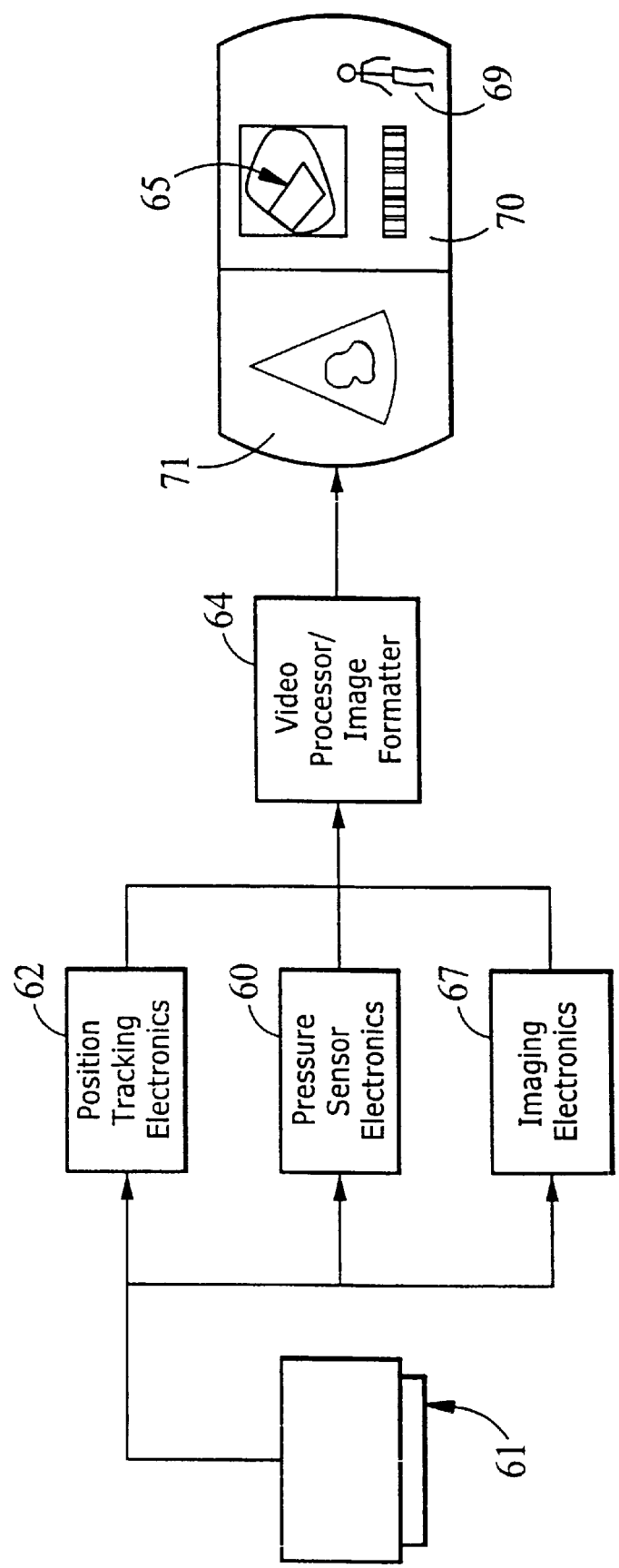
FIG. 13 is a block diagram of electronics used with the scanning head of FIG. 12.

Referring to FIG. 13, position tracking electronics 62 correlates the position information with information from pressure sensors on head 61 to determine a location of the scanner head relative to the tissue being examined. Tracking may be performed with respect to one or more reference points on the patient's body, and can be used to control the angle of scanning head 61. For example, the location of scanning head 61 may be tracked over a breast. This information is translated into an image by image formatter 64 and superimposed on a topographic map 65 generated from pressure information. Pressure sensing electronics 66 and imaging electronics 67 perform the same functions as their counterparts described above.

Figure 14:
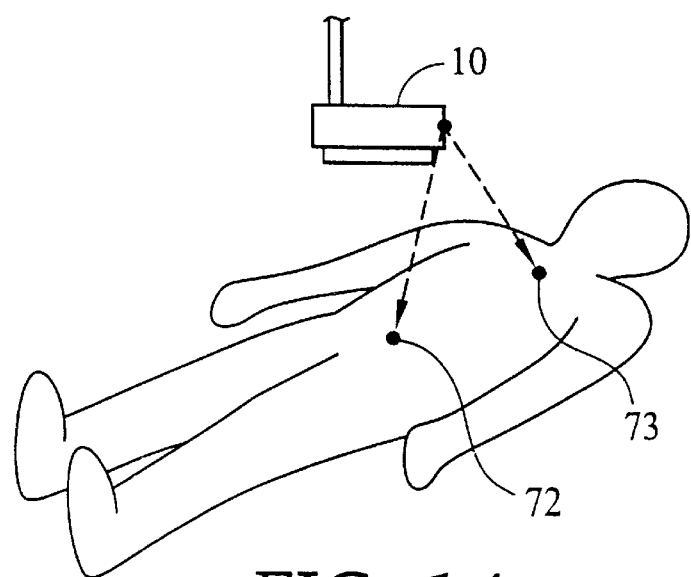
FIG. 14 is a view of a fiducial points on a body and the scanning head of FIG. 12.

The location of scanning head 61 relative to an image 69 of the patient's body is displayed in area 70 of display 71. The location of the scanning head on the patient's body is determined based on fiducial points on the patient's body (72 and 73 in FIG. 14) which are detected using data from position tracking device 62. Examples of fiducial points include the sternal notch, the xiphoid, and nipples. Video processing may also be included in image formatter 64 to show real-time movement of scanning head 61 relative to topographic map 65 and/or the patient's body.

The foregoing describes using a position tracking device in conjunction with both pressure sensors and ultrasound transducers. The invention, however, is not limited to this arrangement. For example, position tracking device 60 could be used on a scanning head that includes only pressure sensors or on a scanning head that includes only ultrasound transducers. Similarly, position tracking device 60 could be used on a scanning head that includes other types of imaging sensors, either alone or in combination with pressure sensors or ultrasound transducers.

4. Using Ultrasound Images to Obtain Tissue Depth

Figure 15:
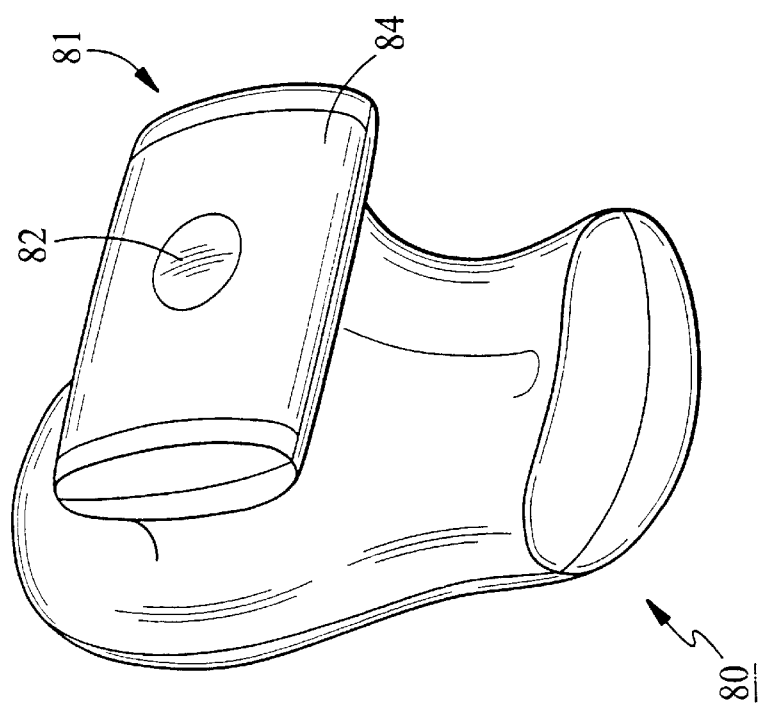
FIG. 15 is a perspective-bottom view of an alternative embodiment of the tissue examination device.

FIG. 15 shows a device 80 which uses ultrasound and pressure sensors to obtain information about underlying bodily tissue. FIG. 15 is a bottom view of device 80, which depicts on area 81 that contacts the patient's skin during examination. As shown, area 81 includes one or more A-mode ultrasound transducers 82 and pressure sensors 84 arranged around the ultrasound transducers. A-mode ultrasound transducers provide position information, but (generally) not image information like other ultrasound transducers. Ultrasound transducers 82 and pressure sensors 84 contact a patient's skin, such as the breast, to obtain information about underlying bodily tissue, including underlying structures such as tumors and lesions.

Ultrasound transducers 82 obtain information that defines cross-sectional slices of the breast tissue. This information is interpreted by a processor or other controller (e.g., DSP 22 of FIG. 5) in device 80 to determine the depth of structures in the (breast) tissue. Pressure sensors 84 obtain information relating to the hardness (or "density") of structures identified using ultrasound. Device 80 uses the information obtained from ultrasound transducers 82 and pressure sensors 84 to provide information to a user about the depth and density of any identified structures.

Figure 16:
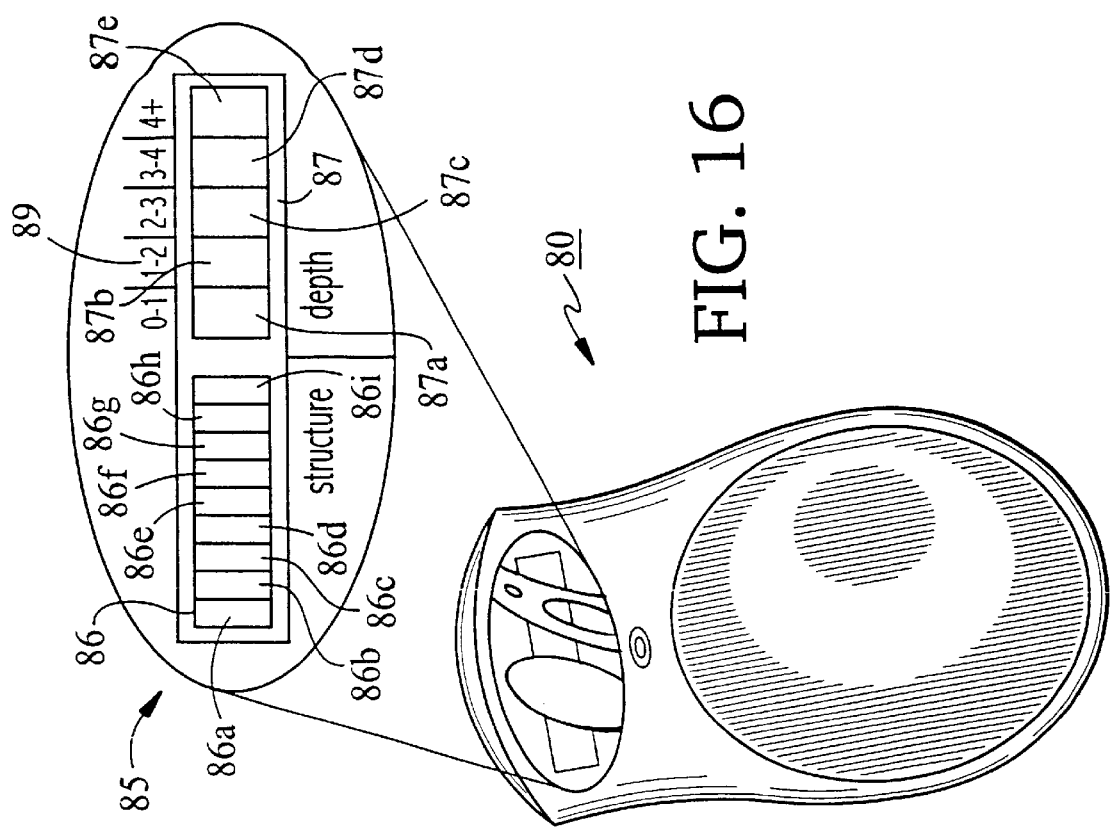
FIG. 16 is a top view of the alternative embodiment of the tissue examination device.

FIG. 16 shows a top view of device 80. Device 80 includes display 85, which has an area 86 for displaying an indication of the density of structures in underlying tissue and an area 87 for displaying the depth of such structures relative to a surface of the underlying tissue. Area 86 is an LED display, in which the density of the underlying tissue is indicated by the number of LEDs 86*a* to 86*i* that are illuminated. For example, relatively dense underlying tissue might cause LEDs 86*a* to 86*h* to illuminate, whereas less dense underlying tissue may cause only LEDs 86*a* and 86*b* to illuminate. Area 87 is also an LED display, which includes a depth indicator scale 89. To indicate the depth of the underlying tissue, LEDs 87*a* to 87*e* illuminate accordingly. For example, for a structure that is "1–2" (centimeters, for example) beneath the surface of the skin, LEDs 87*a* and 87*b* will illuminate.

Figure 17:
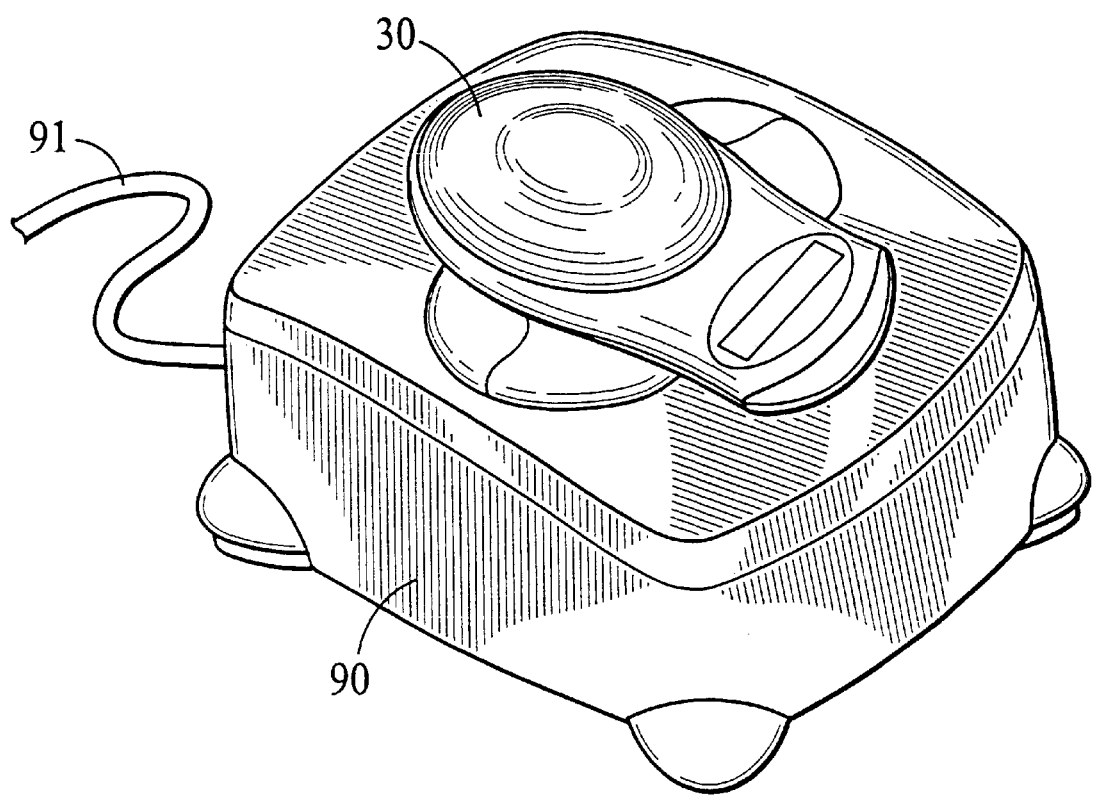
FIG. 17 is a perspective view of the tissue examination device mated to a recalibration station.

Device 80 is a cordless, hand-held device that can be used by a trained clinician. Device 80 is battery operated and can be mated to a recharge and calibration station 90, as shown in FIG. 17. Station 90 includes a connection 91 to a power source, such as a wall outlet, and provides power to device 80 when the two are mated. Station 90 also includes a data link (not shown) to device 80 for recalibration and/or reprogramming. Station 90 may include a modem to transmit images to a remote location over the Internet or other network and/or to download images.

Figure 19:
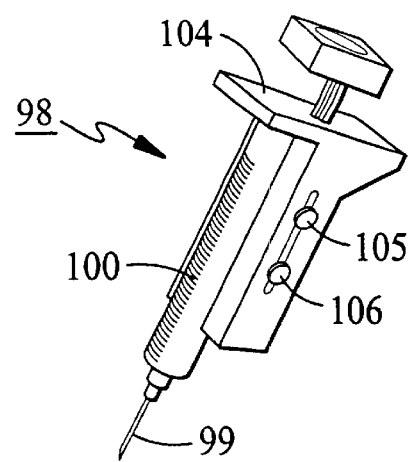
FIG. 19 is a perspective view of a tissue sampling device that attaches to the fixture.
Figure 18:
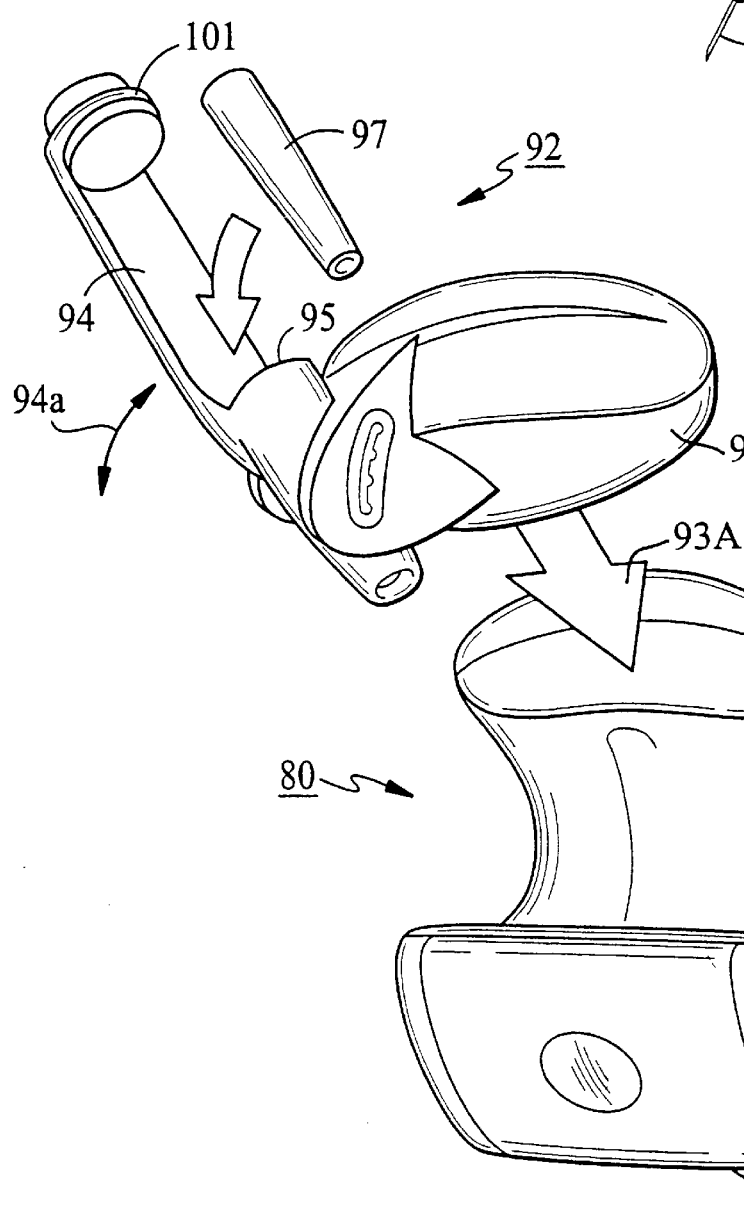
FIG. 18 is a perspective view of a fixture that attaches to the tissue examination device.

As shown in FIG. 18, device 80 also includes an attachable ("snap-on") fixture 92 for guiding a tissue sampling device 98 (see FIG. 19), such as a biopsy device or an aspiration needle for drawing fluid from cysts, to a location on the patient's skin. Fixture 92 includes a receptacle 94 for receiving the tissue sampling device and a bore 95 for receiving a sterile (conical) piece 97. Piece 97 fits flush within, and lines, the bore so that tissue extracted by the tissue sampling device does not contaminate fixture 92. Different size pieces 97 may also be used to adapt to different size biopsy devices. Receptacle 94 is pivotally mounted to portion 93 which snaps onto device 80 in the direction of arrow 93*a*. Receptacle 94 pivots "vertically" in the directions of arrow 94*a*, thereby allowing a user to place the tissue sampling device at different angles relative to the patient's skin (see also FIG. 24, described below).

More specifically, tissue sampling device 98 (with needle 99 internal to syringe 100) is mated to receptacle 94 such that head 101 of fixture 92 fits between shoulders 102 and 104 of tissue sampling device 98. When tissue sampling device 98 is operated (via vacuum set and release controls 105 and 106, respectively) needle 99 is guided through piece 97 to the patient's skin. Once tissue is obtained from the patient, needle 99 is retracted through piece 97 to syringe 100. During this retraction of the needle, tissue from needle 99 may contaminate piece 97. By making piece 97 removable, and thus replaceable, the amount of such contamination to fixture 92 can be reduced. Biopsy devices other than those described above can also be used.

FIGS. 20 and 21 show tissue sampling device 98 mated to receptacle 94. As shown in these figures, fixture 92 includes a slit 110 and a rotatable mechanism 111 which allows receptacle 94 and mated tissue sampling device 98 to rotate horizontally (in the directions of arrow 110*a*) relative to device 80. One advantage of this feature is that tissue sampling device 98 can be operated using either the right hand or the left hand.

Figure 22:
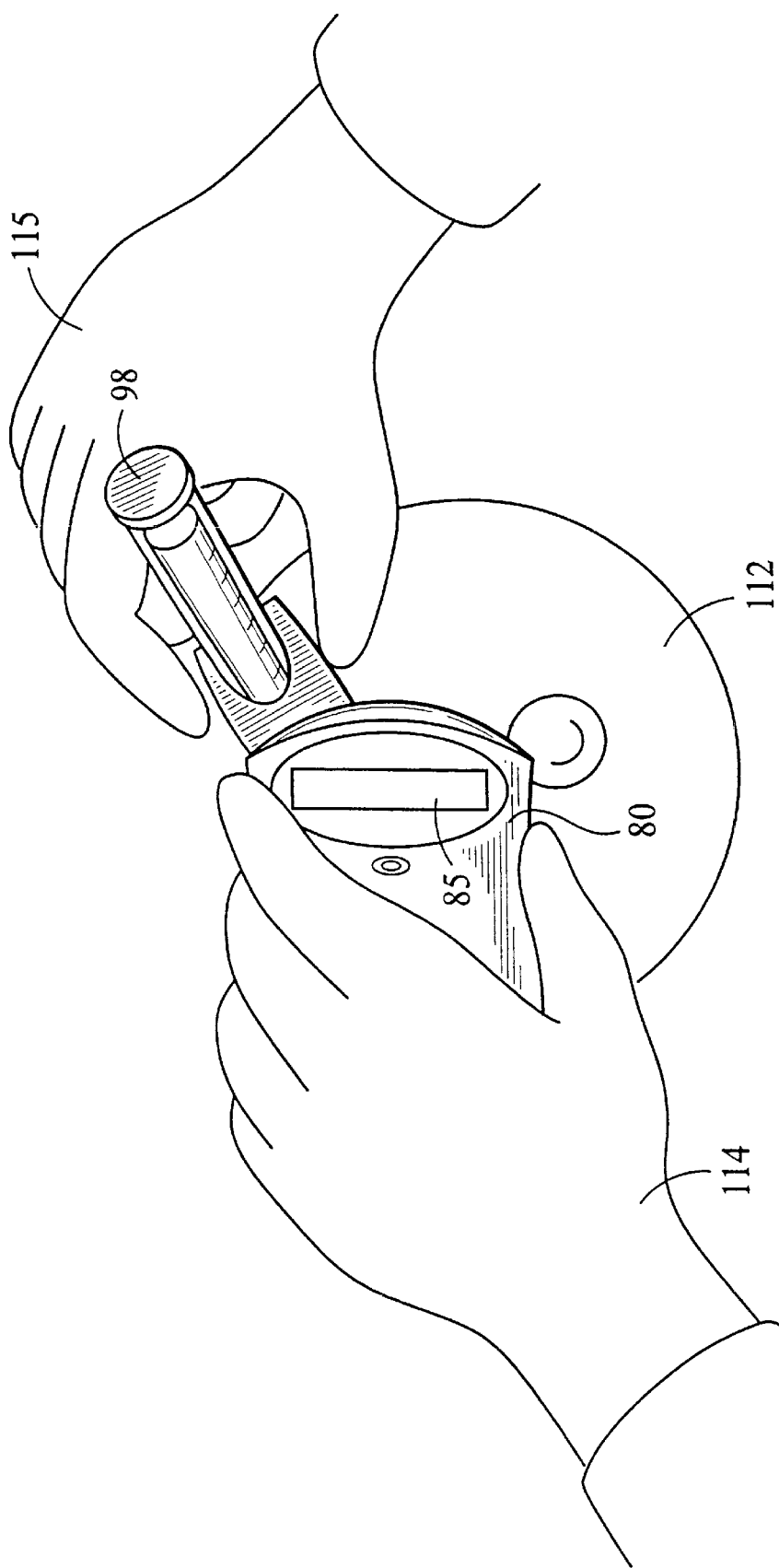
FIG. 22 shows a medical procedure which uses the tissue examination device and the tissue sampling device.

As shown in FIG. 22, device 80 is placed over a patient's breast 112. The user can view information on display 85 while, at the same time, guiding the needle of tissue sampling device 98 to the underlying tissue for which information is displayed. One hand 114 can be used to manipulate device 80 and the other hand 115 can be used to operate tissue sampling device 98.

Figure 23:
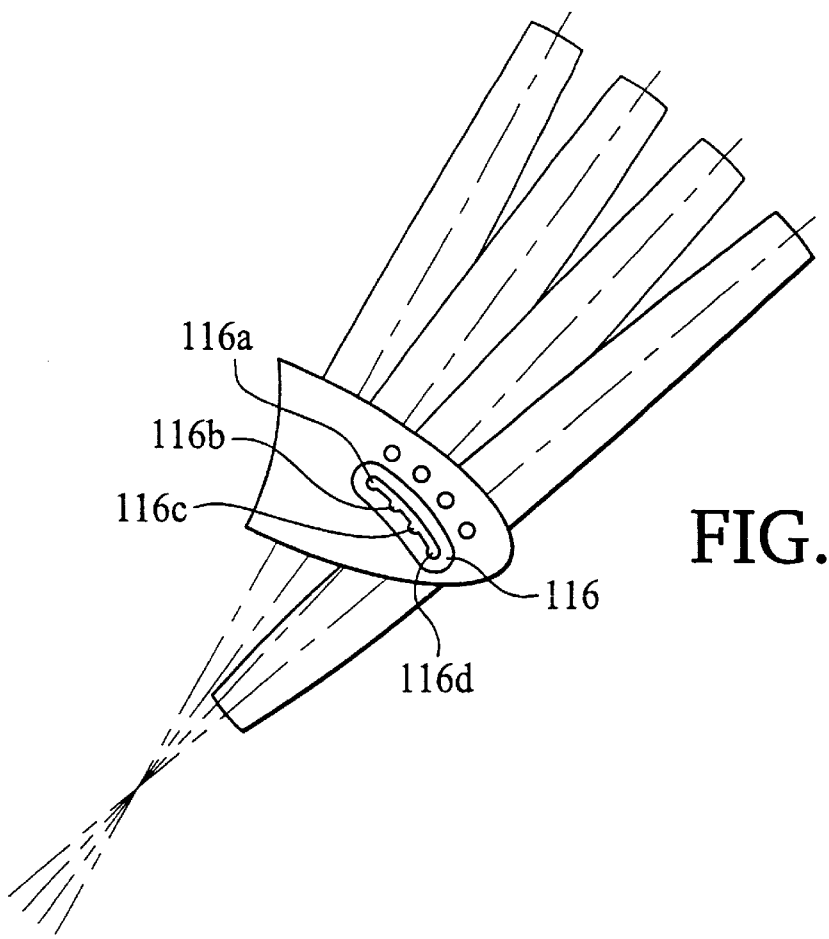
FIG. 23 is a side view of angle settings that are available on the fixture.
Figure 24:
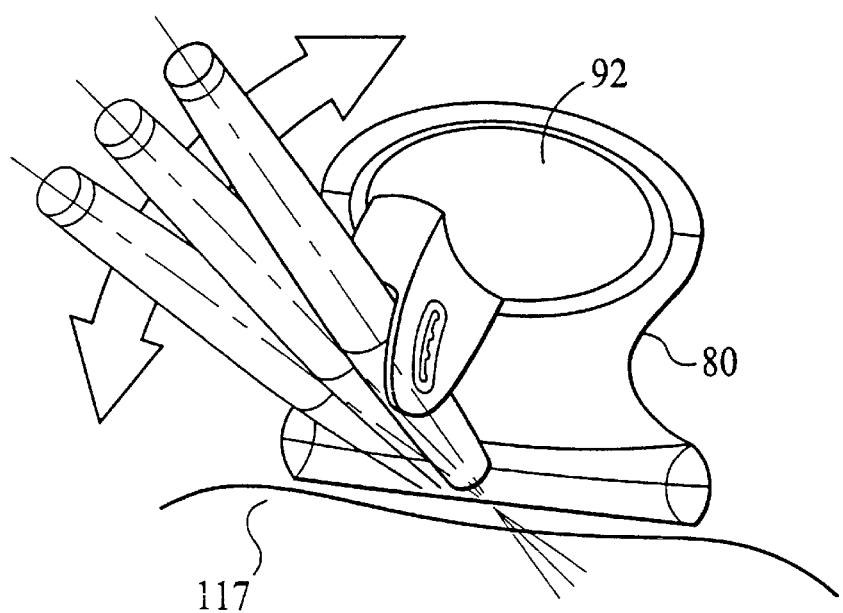
FIG. 24 is a perspective view showing the tissue sampling device and fixture at various angles.

To assist in guiding the needle of tissue sampling device 98 to structures in the underlying tissue, device 80 includes a mechanism 116 for selecting the angle of receptacle 94 and mated tissue sampling device 98 (see FIG. 23). Mechanism 116 includes several settings 116*a* to 116*d*, at which the receptacle and tissue sampling device may be placed relative to the patient's skin. A locking mechanism (not shown) may be used to hold a current setting in place. FIG. 24 shows a perspective view of the various angle settings of receptacle 94 and tissue sampling device 98 relative to tissue 117.

5. Ultrasonic Endoscope with Pressure Sensors

Figure 25:
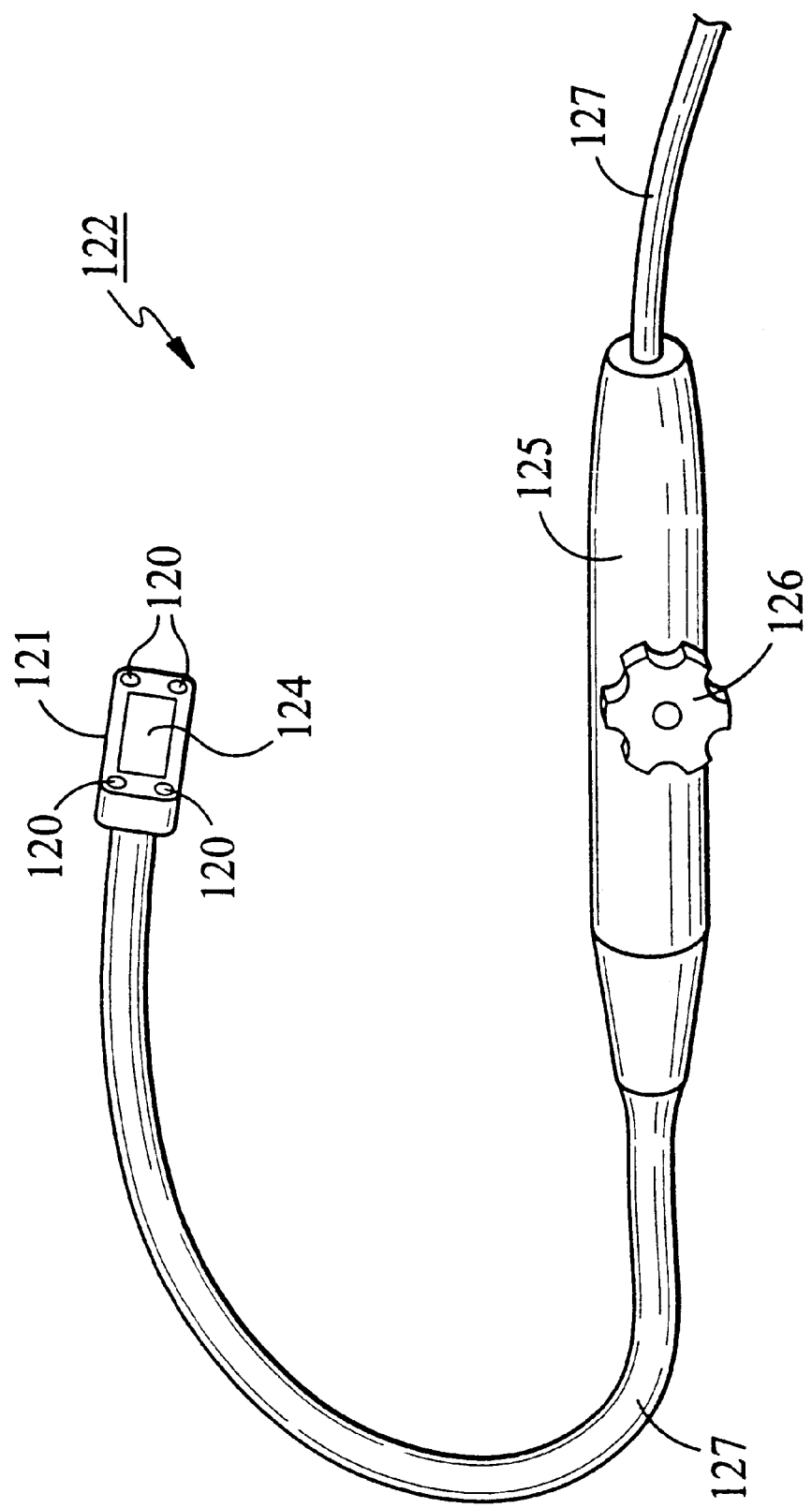
FIG. 25 is a perspective view of an ultrasonic endoscope which includes ultrasound and pressure sensors.

In the embodiment of FIG. 25, pressure sensors 120 are incorporated onto head 121 of ultrasonic endoscope 122. Head 121 also includes ultrasound transducers 124. Pressure sensors 120 are arranged at locations along an outer perimeter of one or more of ultrasound transducers 124. For example, in ultrasonic endoscope 122, there are four pressure sensors that are evenly-spaced around ultrasound transducers 124. The invention, however, is not limited this sensor configuration. Different pressure and ultrasound transducer configurations may be used, including those shown in FIGS. 7 to 9. The pressure sensors and ultrasound transducers operate in the same manner as those in section (1) above (i.e., to monitor and repeat amounts of pressure applied to each pressure sensors during different examinations).

In addition to head 121, ultrasonic endoscope 122 includes handle 125, control knob 126, and guide 127 which includes a data line that connects to a computer that includes the pressure sensing and imaging electronics of FIG. 3, for example. During an endoscopic procedure, guide 127 directs head 121 to bodily tissue that is to be imaged using ultrasound transducers 124. Guide 127 is made from flexible tubing that can be navigated through a patient's body during the procedure. Knobs 126 are used to control the length of guide 127, its tension, and the movement of guide 127 through the patient's body.

Image data from the ultrasound transducers 124 is transmitted to a computer through the data line. Pressure information from pressure sensors 120 is also transmitted. As was the case in the embodiment of FIG. 1, pressure sensors 120 can be used to measure the amount of pressure between head 121 and tissue bordering the structures. This pressure information can be used, for example, to ensure that the same amount of pressure is applied to each pressure sensor during two different examinations of the same tissue (for example, in elastography procedures). The pressure information and images from the ultrasound transducers may be displayed on the display screen or pressure information may be output to an audio or visual display, as described above.

The remaining features and functions associated with ultrasonic endoscope 122 are substantially identical to those described above with respect to FIG. 1. For detailed descriptions of those features and functions, see section (1) above. Furthermore, additional pressure sensors may be incorporated onto head 122 for use in generating a topographic map of the underlying tissue. This structure and function of the pressure sensors in this case is substantially identical to the pressure sensors described in the embodiment of section (2).

The invention can be used in conjunction with any ultrasonic endoscope. For example, the invention can be used in a transesophogeal ultrasonic endoscope, a laparoscope, an intravascular catheter, an ultrasonic gastric endoscope, a duodenoscope, or a colonoscope.

Other embodiments not described herein are also within the scope of the following claims. For example, one or more features from the different embodiments described above can be combined in a single device.

What is claimed is:

1. An apparatus for obtaining image data for a structure through bodily tissue, the apparatus comprising:
   an imaging sensor that, when in use, contacts the bodily tissue to obtain the image data for the structure; and
   a pressure sensor which is oriented in a substantially same direction as the imaging sensor and which, when in use, contacts the bodily tissue to produce a signal, the signal corresponding to an amount of pressure between the pressure sensor and the bodily tissue.

2. The apparatus of claim 1, wherein the imaging sensor comprises an ultrasound transducer.

3. The apparatus of claim 1, wherein the pressure sensor is part of an array of pressure sensors and the imaging sensor is part of an array of imaging sensors, the array of pressure sensors being arranged at locations along an outer perimeter of the array of imaging sensors.

4. The apparatus of claim 3, wherein each pressure sensor produces a signal that is indicative of an amount of pressure between the pressure sensor and the bodily tissue.

5. The apparatus of claim 4, further comprising a processor which analyzes signals from the pressure sensors to determine if an orientation of the pressure sensors is the same as a previous orientation of the pressure sensors.

6. The apparatus of claim 1, further comprising a device which provides an indication of the amount of pressure between the pressure sensor and the bodily tissue based on the signal.

7. The apparatus of claim 6, wherein the device comprises circuitry which receives the signal from the pressure sensor and the image data obtained by the imaging sensor, and which generates the indication and an image of the structure.

8. The apparatus of claim 7, wherein the indication comprises a visual indication.

9. The apparatus of claim 8, wherein the visual indication is implemented using one or more light-emitting diodes which illuminate in accordance with the signal.

10. The apparatus of claim 7, wherein the indication comprises an audio indication.

11. The apparatus of claim 10, wherein the audio indication comprises an audible tone that varies in accordance with the signal.

12. The apparatus of claim 1, wherein the apparatus comprises one of the following: an ultrasonic endoscope, a transesophogeal ultrasonic endoscope, a laparoscope, an intravascular catheter, an ultrasonic gastric endoscope, a duodenoscope, and a colonoscope.

13. An apparatus for obtaining information relating to a structure through bodily tissue, comprising:
   an imaging sensor which, when in use, contacts the bodily tissue to obtain first information relating to the structure; and
   a pressure sensor which is oriented in a substantially same direction as the imaging sensor and which, when in use, contacts the bodily tissue to obtain second information relating to the structure, where the second information differs from the first information.

14. The apparatus of claim 13, wherein the first information indicates a depth of the structure relative to the bodily tissue, and the second information indicates a density of the structure.

15. The apparatus of claim 13, wherein the imaging sensor comprises an A-mode ultrasound transducer.

16. The apparatus of claim 13, further comprising a display for displaying the first information and the second information.

17. The apparatus of claim 13, further comprising a fixture which guides a tissue sampling device to the structure.

18. The apparatus of claim 17, wherein the fixture is movable over a range of angles.

19. A method of obtaining image data for a structure through-bodily tissue, comprising:
   obtaining image data for the structure using an imaging sensor that contacts the bodily tissue; and
   obtaining a signal corresponding to an amount of pressure between the bodily tissue and a pressure sensor in contact with the bodily tissue and oriented in a substantially same direction as the imaging sensor.

20. The method of claim 19, further comprising providing an indication of the amount of pressure between the pressure sensor and the bodily tissue based on the signal.

21. The method of claim 20, wherein the indication comprises a visual indication.

22. The method of claim 20, wherein the indication comprises an audio indication.

23. The method of claim 22, wherein the audio indication comprises an audible tone that varies in accordance with the signal.

24. The method of claim 19, further comprising:
   re-positioning the imaging sensor and the pressure sensor against the bodily tissue;
   obtaining a second signal corresponding to an amount of pressure between the bodily tissue and the pressure sensors; and
   determining if the imaging sensor and the pressure sensor are in a same orientation as during obtaining of the image data based on the signal and the second signal.

25. A method of obtaining information relating to a structure through bodily tissue, comprising:
   obtaining first information relating to the structure using an imaging sensor that contacts the bodily tissue; and
   obtaining second information relating to the structure using a pressure sensor that is oriented in a substantially same direction as the imaging sensor and that contacts the bodily tissue, where the second information differs from the first information.

26. The method of claim 25, wherein the first information indicates a depth of the structure relative to the bodily tissue, and the second information indicates a density of the structure.

27. The method of claim 25, further comprising displaying the first information and the second information.

28. The apparatus of claim 1, wherein the pressure sensor is arranged on a mammography plate.

29. The apparatus of claim 1, wherein the signal is at least indicative of a hardness of the structure.

30. The apparatus of claim 29, wherein the image data is at least indicative of a depth of the structure.

31. The apparatus of claim 1, wherein the image data is at least indicative of a depth of the structure.

32. The apparatus of claim 1, wherein the structure is a tumor or lesion.

33. The apparatus of claim 1, wherein the bodily tissue comprises bodily tissue of a human breast.

34. The apparatus of claim 1, wherein the apparatus is configured such that the image sensor obtains the image data concurrently to the pressure sensor producing the signal.

35. The apparatus of claim 1, wherein the bodily tissue is part of a body, and at least one of the image sensor and the pressure sensor is configured to contact an external surface of the body.

* * * * *